United States Patent
Wang et al.

(10) Patent No.: US 8,751,165 B2
(45) Date of Patent: Jun. 10, 2014

(54) ERROR CORRECTING METHOD OF TEST SEQUENCE, CORRESPONDING SYSTEM AND GENE ASSEMBLY EQUIPMENT

(75) Inventors: Jun Wang, Shenzhen (CN); Huanming Yang, Shenzhen (CN); Jian Wang, Shenzhen (CN)

(73) Assignee: BGI Tech Solutions Co., Ltd. (CN)

( * ) Notice: Subject to any disclaimer, the term of this patent is extended or adjusted under 35 U.S.C. 154(b) by 368 days.

(21) Appl. No.: 13/132,038

(22) PCT Filed: Dec. 11, 2009

(86) PCT No.: PCT/CN2009/001426
§ 371 (c)(1),
(2), (4) Date: Aug. 11, 2011

(87) PCT Pub. No.: WO2010/066114
PCT Pub. Date: Jun. 17, 2010

(65) Prior Publication Data
US 2011/0295784 A1    Dec. 1, 2011

(30) Foreign Application Priority Data
Dec. 12, 2008   (CN) .......................... 2008 1 0218340

(51) Int. Cl.
*G01N 33/48* (2006.01)
*G06F 19/00* (2011.01)
*G06F 19/24* (2011.01)

(52) U.S. Cl.
CPC ..................................... *G06F 19/24* (2013.01)
USPC .............................................. 702/19; 702/20

(58) Field of Classification Search
CPC ..................................................... G06F 19/24
See application file for complete search history.

(56) References Cited

FOREIGN PATENT DOCUMENTS

CN   1360057   7/2002

OTHER PUBLICATIONS

International Search Report mailed on Mar. 25, 2010 for International Application No. PCT/CN2009/001426 filed Dec. 11, 2009.
Song et al., Detection and analysis of complete genome sequence of Yersinia pestis human-avirulent strain 91001, Med J. Chin PLA, vol. 9, pp. 192-199 (Mar. 2004)—English Abstract.
Zhang et al., "An approach based on fast Walsh transform and heuristic search to DNA fragments assembly," Journal of Communication and computer, vol. 4, pp. 5-8, (Sep. 2007)—English Abstract.
Song, et al., "Complete Genome Sequence of Yersinia pestis Strain 91001, an Isolate Avirulent to Humans," DNA Research, vol. 11, pp. 179-197 (2004).

*Primary Examiner* — Anna Skibinsky
(74) *Attorney, Agent, or Firm* — Wilmer Cutler Pickering Hale and Dorr LLP

(57) ABSTRACT

The present invention provides an error correcting method of test sequence, which involves receiving test sequences, configuring high frequency short string list based on a preset high frequency threshold value, traversing each received test sequence, searching an area with the largest number of continuous high frequency short strings on each test sequence in combination with high frequency short string list, configuring whole left sequence and/or right sequence of high frequency short strings at left side and/or right side of searched area according to corresponding received test sequence and high frequency short string list, and constituting corresponding test sequence according to configured left and/or right sequence and searched area. The present invention also provides corresponding error correcting system of test sequence and gene assembly equipment.

5 Claims, 3 Drawing Sheets

ERROR CORRECTING METHOD OF TEST SEQUENCE, CORRESPONDING SYSTEM AND GENE ASSEMBLY EQUIPMENT

This application is a U.S. National Phase application under 35 U.S.C. §371 of International Patent Application No. PCT/CN2009/001426 filed Dec. 11, 2009, which claims priority to Chinese Application Ser. No.: 200810218340.6 filed Dec. 12, 2008, the contents of which applications are hereby incorporated by reference in their entireties.

TECHNICAL FIELD

The present invention relates to the technical field of gene engineering, and more specifically, to an error correcting method of test sequence, a corresponding system and a gene assembly equipment.

DESCRIPTION OF THE RELATED ART

Based on the existing gene sequencing technology, there is a possibility of making errors in sequencing of the bases. The error in sequencing has an influence on the subsequent data analysis, short sequence assembly, and etc. Because the probability that an errorless sequence contains low frequency short strings is very low under a deep sequencing depth, the existing error correcting strategy is to simply screen out low frequency short strings in a test sequence and delete sequences that contain a certain proportion of low frequency short strings. In fact, no effective error correction is done and it leads to a low utilization of test sequences.

SUMMARY OF THE INVENTION

An object of an embodiment of the present invention is to provide an error correcting method of test sequence, which is intended to solve the following problem of low utilization of test sequences in the existing error correcting method of test sequence.

An embodiment of the present invention is implemented by an error correcting method of test sequence comprising the steps of:

receiving test sequences, and configuring a high frequency short string list based on a preset high frequency threshold value;

traversing each received test sequence, and searching for an area with the largest number of continuous high frequency short strings on each test sequence in combination with the high frequency short string list;

configuring a left sequence that consists solely of high frequency short strings at left side of the searched area and/or configuring a right sequence that consists solely of high frequency short strings at right side of the searched area according to corresponding received test sequence and the high frequency short string list; and combining the area and the configured left and/or right sequence into a corresponding test sequence.

Another object of an embodiment of the present invention is to provide an error correcting system of test sequence comprising:

a statistical unit of high frequency short string, for receiving test sequences, and configuring a high frequency short string list based on a preset high frequency threshold value;

a searching unit of high frequency area, for traversing each received test sequence, and searching for an area with the largest number of continuous high frequency short strings on each test sequence in combination with the high frequency short string list;

a sequence configuring unit, for configuring a left sequence that consists solely of high frequency short strings at left side of the searched area and/or configuring a right sequence that consists solely of high frequency short strings at right side of the searched area according to corresponding received test sequence and the high frequency short string list; and a sequence combining unit, for combining the area and the configured left and/or right sequence into a corresponding test sequence.

Another object of an embodiment of the present invention is to provide a gene assembly equipment comprising the above-mentioned error correcting system of test sequence.

In embodiments of the present invention, a high frequency short string list is configured based on a preset high frequency threshold value, sequences of areas with discrete high frequency short strings in each test sequence are recombined into a sequence of continuous high frequency short strings according to the configured high frequency short string list. The recombined sequence retains the number and length of the original test sequences as much as possible, improves the utilization of the sequence, and it is proved via experiments that great improvements are achieved on the proportion and depth of errorless sequences in the error-corrected sequence. The error-corrected sequence may be divided into longer high frequency short strings and fewer high frequency short strings may be obtained, thereby reducing the use of memory during a subsequent short sequence assembly.

DETAILED DESCRIPTION OF THE PREFERRED EMBODIMENT

In order for the object, technical solutions and advantages of the present invention to be better understood, a further detailed explanation of the present invention will be given below in combination with drawings and embodiments. It should be understood that specific embodiments described herein is solely for explaining the present invention, but not for limiting the present invention.

In an embodiment of the present invention, a high frequency short string list is configured based on a preset high frequency threshold value, and sequences of areas with discrete high frequency short strings in each test sequence are recombined into a sequence of continuous high frequency short strings according to the configured high frequency short string list.

Figure 1:
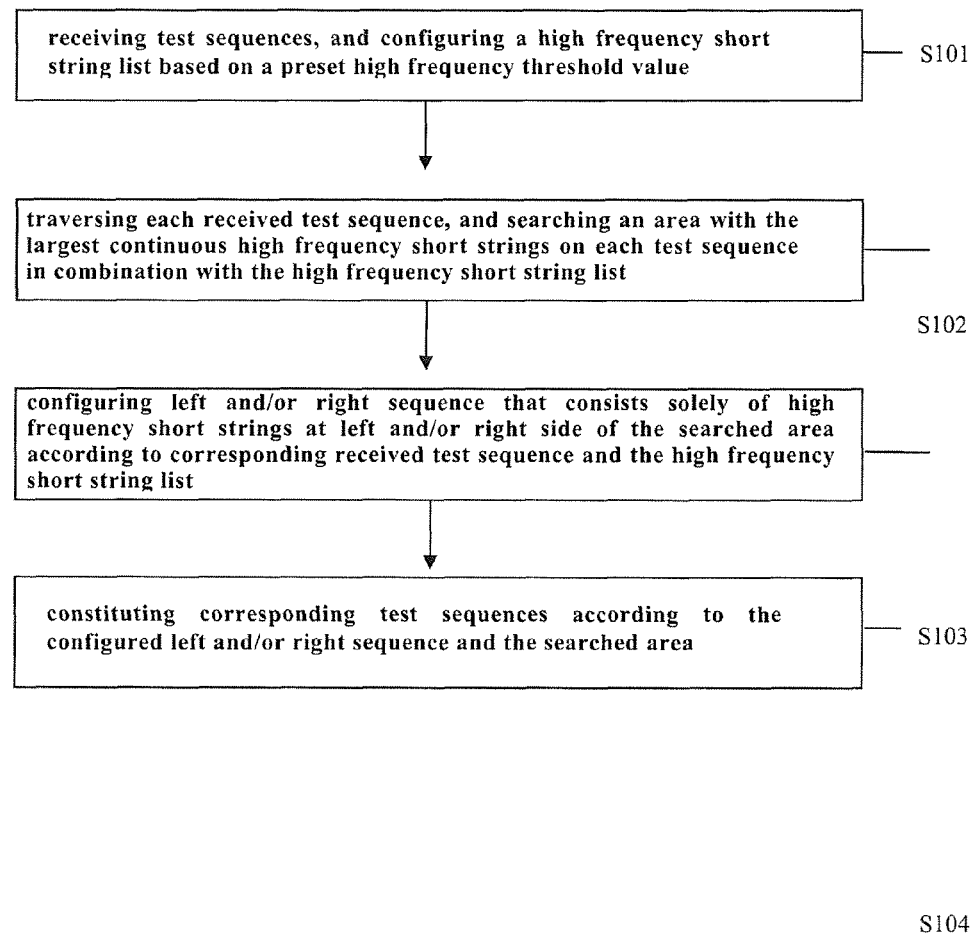
FIG. 1 is a flowchart of an error correcting method of test sequence provided according to an embodiment of the present invention.

FIG. 1 illustrates a flowchart of an error correcting method of test sequence provided according to an embodiment of the present invention. The details are as follows:

Step S101: receiving test sequences, and configuring a high frequency short string (kmer) list based on a preset high frequency threshold value;

Step S102: traversing each received test sequence, and searching for an area with the largest number of continuous high frequency short strings on each test sequence in combination with the high frequency short string list;

Step S103: configuring a left sequence that consists solely of high frequency short strings at left side of the searched area and/or configuring a right sequence that consists solely of high frequency short strings at right side of the searched area according to corresponding received test sequence and the high frequency short string list; and Step S104: combining the area and the configured left and/or right sequence into a corresponding test sequence.

In an embodiment of the present invention, the above step S101 is detailed as follows:

1. receiving test sequences and dividing each received test sequence into short strings with a preset length on the basis of one-base-by-one-base;

2. configuring a high frequency short string list, based on the divided short strings which appears at a number larger than the preset high frequency threshold value.

Here, with regard to the length of each received test sequence, there is no limit on the logic of processing procedure, but it is generally below 200 base pairs (bp). The preset length n of short strings is 17 bp, and the preset high frequency threshold value is 5 (times). It is assumed that a short string which appears more than 5 times is a high frequency short string. The high frequency short strings are added to the high frequency short string list. Of course, the preset length n of short strings can be any integer from 1 to the base length of the test sequence. However, when n is larger than 17 bp, the memory and computing time will increase; and when n is less than 17 bp, the effect of error correcting is not good. So, n is preferably 17 bp. The high frequency threshold value may be determined according to the frequency distribution of the divided short strings. Theoretically, there should be two peaks in the frequency distribution: the first one is caused by sequencing error, and the second one is caused by the sequencing depth. So, the first valley value is usually used as the high frequency threshold value.

Next, an area with the largest number of continuous high frequency short strings on each test sequence is searched, the step S102 is detailed as follows:

1. traversing each received test sequence, and searching for an area with the continuous high frequency short strings on each test sequence in combination with the high frequency short string list. That is, short strings of the test sequence are sequentially traversed. If a short string appears in the high frequency short string list, the short string is considered as a high frequency short string; otherwise, the short string is considered as a non-high frequency short string. After traversing each test sequence in this way, an area with continuous high frequency short strings corresponding to each test sequence can be obtained.

2. taking the searched longest area on each test sequence as the area with the largest number of continuous high frequency short strings. Here it is assumed that the area with the largest number of continuous high frequency short strings on each test sequence is [s1, s2], wherein s1 and s2 are the numbers of bases that the starting base and the ending base of the searched longest area with the continuous high frequency short strings apart from the first base of the corresponding test sequence.

If a test sequence is $X_1 X_2 X_3 \ldots X_{l_n-1} X_{l_n}$ where $l_n$ is the base length of the test sequence, $X_i$, denotes the i-th base of the test sequence. The longest area with the continuous high frequency short strings of the test sequence is [26, 46], that is, $X_{26} X_{27} X_{46}$ is the longest high frequency sequence in the test sequence.

Figure 2:
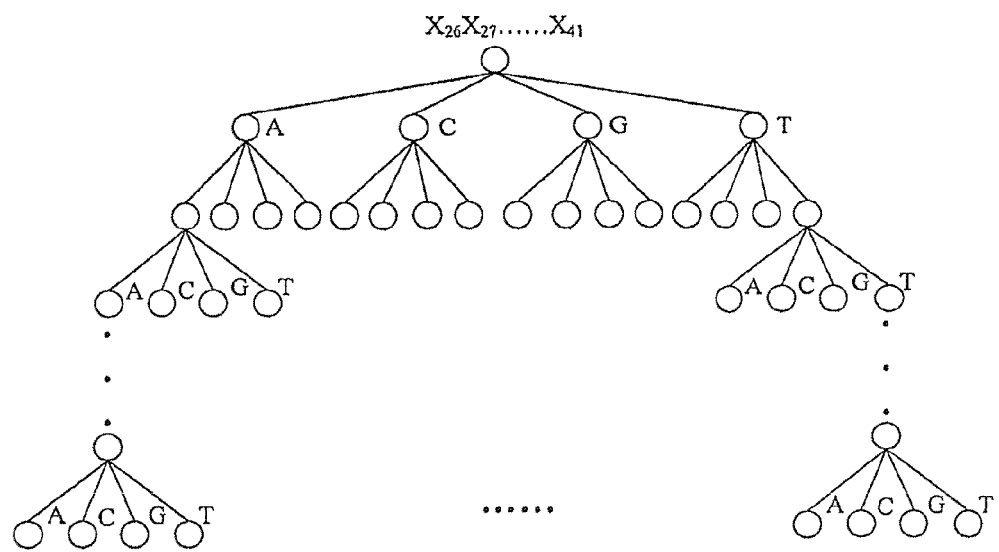
FIG. 2 is a schematic structural diagram of a left side tree provided according to an embodiment of the present invention.

Then, based on the original test sequence and the high frequency short string list, a sequence that consists solely of high frequency short strings is configured at the left side and at the right side of [s1, s2], respectively. The above step S103 is detailed as follows:

Step 1: taking a sequence with the length of n−1, starting from the s1-th base of the corresponding test sequence as the root node of a tree, and configuring a left side tree having the depth of s1 with four types of bases A, C, G, T as the leaves of each node. The configured tree is as shown in FIG. 2. Here, the depth s1 is 26;

Step 2: traversing the left side tree, searching for a path that consists solely of high frequency short strings, and configuring a left sequence that consists solely of high frequency short strings from a leaf node along the path upwardly.

Here, the tree is traversed downward from the root node. The root node is a sequence $N_1$ with the length of n−1, and the sub-nodes $L_1$ are the four types of bases A, C, G, T in order. It is determined whether the short string $kmer_1 = L_1 + N_1$ is a high frequency short string, i.e., whether the short string is in the high frequency short string list. If not, the corresponding path of the corresponding base is ended; and if yes, it is further determined whether the value of $L_1$ is equal to the value of the corresponding base $X_{s1-1}$, in the corresponding test sequence $X_1 X_2 X_3 \ldots X_{49} X_{50}$. If yes, the level-1 node score $score_1$ is set as 0t, otherwise the level-1 node score $score_1$ is set as 1. Further, a sequence $N_2$ with the length of n−1 is taken at the left end of $kmer_1$. The short string $kmer_2 = L_2 + N_2$ is analyzed in the above manner, and the sub-nodes $L_2$ thereof are the four types of bases A, C, G, T in order. The iteration and analysis is performed towards leaf nodes according to this rule. After the iteration, a path with the minimum total score $$score = \sum_{i=1}^{s1-1} score_i$$

is located, wherein the $score_i$, is the level-i node score in the corresponding path. The located minimum path is the path that consists solely of high frequency short strings. A sequence obtained by traversing from a leaf node to the root node is the left sequence that consists solely of high frequency short strings to be configured. Of course, if a plurality of paths with equal minimum total scores are obtained after the iteration, one of them is selected randomly. Then the left sequence consisting solely of high frequency short strings to be configured is obtained by traversing from the leaf node towards the root node. Of course, the tree may also be traversed from bottom to top to search for a path consisting solely of high frequency short strings.

Step 3: taking a sequence with the length of n−1 starting from the s2-th base of the corresponding test sequence as a root node of a tree, and configuring a right side tree having the depth of $l_n - (s2-1)$ with four types of bases A, C, G, T as the leaves of each node, where the $l_n$ is the base length of the test sequence. The tree is configured in the same manner as in the above step 1, and the description thereof will be omitted here.

Step 4: traversing the right side tree, searching for a path consisting solely of high frequency short strings, and configuring a right sequence consisting solely of high frequency short strings from the root node along the path downwardly.

The minimum path is searched in the same manner as in the above step 2, and the detailed description thereof will be omitted here.

After sequences consisting solely of high frequency short strings at the left side and at the right side of the corresponding test sequence are obtained, the obtained left sequence is added at the left side of the corresponding longest high frequency sequence $X_{s1}X_{s1+1} \ldots X_{s2}$, and the obtained right sequence is added at the right side of the corresponding longest high frequency sequence $X_{s1}X_{s1+1} \ldots X_{s2}$. That is, the corresponding test sequence after error correcting is obtained.

Of course, if the area with the largest number of continuous high frequency short strings in a corresponding test sequence is $[1, s2]$ or $[s1, 1_n]$, i.e., the area is at the left end or right end of the test sequence, it is only needed to configure a right sequence consisting solely of high frequency short strings at the right side of $[1, s2]$ or configure a left sequence consisting solely of high frequency short strings at the left side of $[s1, 1_n]$. Under this circumstance, when the corresponding test sequence is recovered, it is only needed to add the obtained left sequence at the left side of the corresponding longest high frequency sequence or add the obtained right sequence at the right side of the corresponding longest high frequency sequence.

The technical effect of the error correcting method of test sequence of the present invention is explained by an experiment. In this experiment, the method provided by the above embodiment of the present invention is used to perform error correction on Human control BAC and African Human genome. Data before error correction is as shown in Table 1 and data after error correction is as shown in Table 2:

TABLE 1

| Gene Sequence | Total Numbers of Sequences | % of Errorless Sequences | Depth of Errorless Sequences | Number of Short Strings with Base Length of 25 |
|---|---|---|---|---|
| Human BAC | 6418794 | 64.13 | 830 | 17255027 |
| Human genome | 3594519008 | 67.84 | 29 | 7407311848 |

TABLE 2

| Gene Sequence | Total Numbers of Sequences | % of Errorless Sequences | Depth of Errorless Sequences | Number of Short Strings with Base Length of 25 |
|---|---|---|---|---|
| Human BAC | 4955988 | 95.31 | 952 | 301824 |
| Human genome | 3298690572 | 91.87 | 37 | 3058863566 |

As seen in Tables 1 and 2, after the error correction, the proportion of errorless sequences in the test sequences is increased by approximately 30%, and the depth of errorless sequences is increased by approximately 10%.

The following is an estimate of memory resource required when the error correcting method of test sequence provided by the embodiment of the present invention is used to implement the error correction process. When the short string is of 17 base length, a memory of 16G is occupied. Additionally, because all the sequences stored in one file has to be read into the memory when each thread is processing the file, assuming that one test sequence occupies 50 bytes, the name of the sequence occupies 50 bytes and each file stores 10M test sequences, then 1G memory is required to be occupied to perform error correction on the test sequences stored in one file. Moreover, each thread has a separate dynamic scheduling table that occupies 1G memory, so one thread will occupy 2G memory. When 4 threads run by default, 24G memory will be occupied.

In addition, the time consumed by calculating frequencies of short strings and outputting a frequency list varies, depending on the size of the file and the input/output conditions. It takes about 100 s to process one file. The African human genome has a total of 606 files. At the first step, it takes 15 h to output a frequency list.

After the error correcting method of test sequence provided by the embodiment of the present invention is used to perform error correction on a test sequence, the memory occupied by a subsequent assembly genome of short sequences may be reduced by 50%. Also, low frequency short strings are merged by high frequency short strings after the error correction (i.e. low frequency short strings are corrected into high frequency short strings), and the subsequent assembly strategy needs to only divide the sequence into longer short strings (e.g. 25 base length) for assembly, thus the use of memory is reduced.

Further, in order to improve the speed of error correction, a plurality of threads may be used to split and process all the files to be error corrected. It takes about 1000 s to process one file, and it takes 1000 s*100/4=25000 s=7 h to process 100 files using 4 threads. At the second step, when 6 threads are used to split and process 606 files of the African human genome into 6 subset, it takes only 7 h, and it takes a total of 22 h to perform the error correction.

Those skilled in the art would understand that it is possible that all or a part of those steps in the above method provided by the embodiment can be implemented by relevant hardware instructed by programs. Said programs may be stored in a computer readable storage medium, such as ROM/RAM, magnetic disk, optical disk, and etc. The program is configured to perform the following steps:

1. receiving test sequences, and configuring a high frequency short string list based on a preset high frequency threshold value;

2. traversing each received test sequence, and searching for an area with the largest number of continuous high frequency short strings on each test sequence in combination with the high frequency short string list;

3. configuring a left sequence that consists solely of high frequency short strings at left side of the searched area and/or configuring a right sequence that consists solely of high frequency short strings at right side of the searched area according to corresponding received test sequence and the high frequency short string list; and 4. combining the area and the configured left and/or right sequence into a corresponding test sequence.

Figure 3:
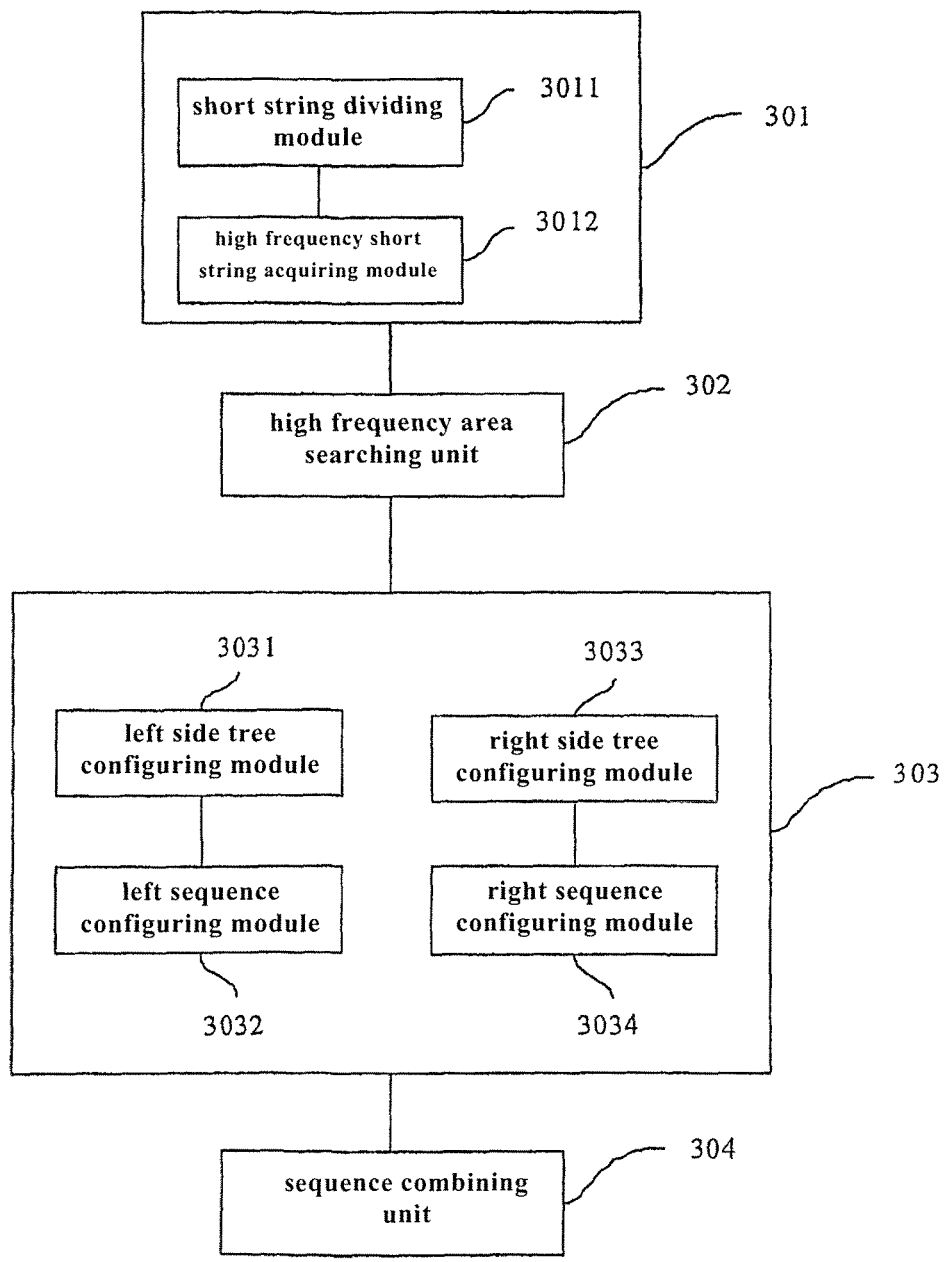
FIG. 3 is a structural diagram of an error correcting system of test sequence provided according to an embodiment of the present invention.

FIG. 3 illustrates the structure of an error correcting system of test sequence provided by an embodiment of the present invention. For ease of explanation, only parts related to the embodiment of the present invention are illustrated.

The system may be used in a gene assembly equipment. It may be a software unit, a hardware unit or a combination of a software unit and a hardware unit operating in the equipment, and may also be integrated into the equipment or application system operating in the equipment as independent component, in which:

A statistical unit 301 of high frequency short string, for receiving test sequences, and configuring a high frequency short string list based on a preset high frequency threshold value. The implementation thereof is as above mentioned and the detailed description thereof is omitted.

A searching unit 302 of high frequency area, for traversing each received test sequence, and searching for an area with the largest number of continuous high frequency short strings on each test sequence in combination with the high frequency short string list.

A sequence configuring unit 303, for configuring a left sequence that consists solely of high frequency short strings at left side of the searched area and/or configures a right sequence that consists solely of high frequency short strings at right side of the searched area according to corresponding received test sequence and the high frequency short string list.

A sequence recovering unit 304, for combining the area and the configured left and/or right sequence into a corresponding test sequence.

Wherein the statistical unit 301 of high frequency short string comprises:

a short string dividing module 3011, for receiving test sequences and dividing each received test sequence into short strings with a preset length on the basis of one-base-by-one-base;

a high frequency short string acquiring module 3012, for configuring the high frequency short string list based on divided short strings which appears at a number larger than the preset high frequency threshold value. The implementation thereof is as above mentioned and the detailed description thereof is omitted.

Furthermore, the sequence configuring unit 303 comprises:

a left side tree configuring module 3031, for taking a sequence with the length n−1 starting from the s1-th base of the corresponding test sequence as a root node of a tree, and configuring a tree having the depth of s1 with four types of bases A, C, G, T as the leaves at each node. The definition of s1 and n and the implementation of the left side tree configuring module 3031 are mentioned as above and the description thereof is omitted.

a left sequence configuring module 3032, for traversing the left side tree, searching for a path consisting solely of high frequency short strings, and configuring a left sequence consisting solely of high frequency short strings from a leaf node along the path upwardly. The implementation thereof is mentioned as above and the description thereof is omitted.

a right side tree configuring module 3033, for taking a sequence with the length of n−1 starting from the s2-th base of the corresponding test sequence as a root node of a tree, and configuring a right side tree having the depth of $l_n-(s2-1)$ with four types of bases A, C, G, T as the leaves at each node, wherein the definition of s2, n and $l_n$ and the implementation of the right side tree configuring module 3033 are mentioned as above and the description thereof is omitted.

a right sequence configuring module 3034, for traversing the right side tree, searching for a path consisting of high frequency short strings solely, and configuring a right sequence consisting of high frequency short strings solely from the root node along the path downwardly. The implementation thereof is mentioned as above and the description thereof is omitted.

In an embodiment of the present invention, a high frequency short string list is configured based on a preset high frequency threshold value, sequences of areas with discrete high frequency short strings in each test sequence are recombined into a sequence of continuous high frequency short strings according to the configured high frequency short string list. The recombined sequence retains the number and length of the original test sequences, improves the utilization of the sequence, and it is proved via experiment that great improvements are achieved on the proportion and depth of errorless sequences in the error-corrected sequence. The error-corrected sequence may be divided into longer high frequency short strings and the use of memory during a subsequent short sequence assembly is reduced.

The present invention also provides a gene assembly equipment containing the above mentioned error correcting system of test sequence, wherein the memory occupied during the assembly will be less than the memory occupied when the test sequence not subject to error correction. This is because the error corrected sequence may be divided into high frequency short strings with longer base length for assembly and fewer high frequency short strings may be obtained, thereby reducing the use of memory.

The above embodiments are only preferable ones of the present invention, but not for limiting the present invention. Any modifications, alternations and variations, etc. within the spirit and principle of the present invention are intended to fall within the protection scope of the present invention.

What is claimed is:

1. A computer-implemented method for correcting test sequences comprising:

dividing, using a processor, a test sequence into short strings with a preset length on the basis of one-base-by-one-base, wherein the preset length is n;

configuring a high frequency short string list based on the short strings using a processor, wherein the high frequency short string list consists of short strings with a frequency of occurrence larger than a preset high frequency threshold value;

traversing the test sequence using a processor, and searching for an area [s1, s2] with the largest number of continuous high frequency short strings on each test sequence by referring to the high frequency short string list; wherein s1, s2 are respectively the starting base and the ending base of the searched area with the largest number of continuous high frequency short strings; wherein the test sequence has a length of $l_n$ and an area of [s1, s2];

taking a sequence with length of n−1 starting from the s1-th base of the test sequence as a root node of a tree, and using a processor to configure a left side tree having depth of s1 with four types of bases A, C, G, T as the leaves of each node;

traversing from a leaf node on the left side tree, using a processor, searching for a path that consists of high frequency short strings, and configuring a left sequence that consists of high frequency short strings along the path upwardly;

taking a sequence with the length of n−1 starting from the s2-th base of the test sequence as a root node of a tree, and using a processor to configure a right side tree having depth of $l_n-(s2-1)$ with four types of bases A, C, G, T as the leaves of each node;

traversing from the root node on the right side tree, using a processor, searching for a path consisting of high frequency short strings, and configuring a right sequence consisting solely of high frequency short strings along the path downwardly;

and using a processor to recover the test sequence according to the left sequence and/or the right sequence and the area [s1, s2] by adding the left sequence at the left side of the area [s1, s2] and/or adding the right sequence at the right side of the area [s1, s2].

2. The method according to claim 1, wherein the preset high frequency threshold value is determined according to a frequency distribution of the short strings with the preset length, wherein the preset length is 17 bases in length.

3. The method according to claim 1, wherein the length of the test sequence is equal to or less than 200 bases.

4. A computer-implemented system for correcting test sequences comprising:

hardware instructed by a program for dividing a test sequence into short strings with a preset length on the basis of one-base-by-one-base, wherein the preset length is n;

hardware instructed by a program for configuring a high frequency short string list based on the short strings, wherein high frequency short string list consists of short strings with a frequency of occurrence larger than the preset high frequency threshold value;

hardware instructed by a program for traversing the test sequence, and searching for an area [s1, s2] with the largest number of continuous high frequency short strings on each test sequence by referring to the high frequency short string list; wherein s1, s2 are respectively the starting base and the ending base of the searched area with the largest number of continuous high frequency short strings; wherein the test sequence has a length of $l_n$ and an area of [s1, s2];

hardware instructed by a program for configuring a left side tree by taking a sequence with the length n−1 starting from the s1-th base of the corresponding test sequence as a root node of a tree, and configuring a left side tree having the depth of s1 with four types of bases A, C, G, T as the leaves of each node;

hardware instructed by a program for traversing from a leaf node on the left side tree, searching for a path consisting of high frequency short strings, and configuring a left sequence consisting of high frequency short strings along the path upwardly;

hardware instructed by a program for configuring a right side tree by taking a sequence with the length of n−1 starting from the s2-th base of the test sequence as a root node of a tree, and configuring a right side tree having the depth of $l_n$−(s2−1) with four types of bases A, C, G, T as the leaves of each node;

hardware instructed by a program for traversing from the root node on the right side tree, searching for a path consisting of high frequency short strings, and configuring a right sequence consisting of high frequency short strings from the root node along the path downwardly; and hardware instructed by a program for recovering the test sequence according to the left sequence and/or right sequence and the area [s1, s2] by adding the left sequence at the left side of the area [s1, s2] and/or adding the right sequence at the right side of the area [s1, s2].

5. The system according to claim 4, wherein the preset high frequency threshold value is determined according to a distribution frequency of the short strings with the preset length, wherein the preset length is 17 bases in length.

* * * * *